United States Patent [19]

Szabo et al.

[11] Patent Number: 4,676,122
[45] Date of Patent: Jun. 30, 1987

[54] FAIL-SAFE MECHANICAL DRIVE FOR SYRINGE

[75] Inventors: Anthony W. Szabo, Livingston, N.J.; Robert E. Hunt, Duxbury, Mass.

[73] Assignee: Daltex Medical Sciences, Inc., West Orange, N.J.

[21] Appl. No.: 820,571

[22] Filed: Jan. 16, 1986

Related U.S. Application Data

[63] Continuation-in-part of Ser. No. 620,936, Jun. 15, 1984, Pat. No. 4,602,700.

[51] Int. Cl.[4] .................. A61M 5/20; F03G 1/00; F16H 35/06
[52] U.S. Cl. .................. 74/625; 185/38; 185/39; 222/326; 222/333; 604/135; 604/154
[58] Field of Search .............. 185/37, 38, 39, DIG. 1; 222/326, 333; 604/135, 154, 155; 128/DIG. 1, 655; 74/625

[56] References Cited

U.S. PATENT DOCUMENTS

| | | | |
|---|---|---|---|
| 3,621,939 | 11/1971 | Hughes | 185/DIG. 1 X |
| 4,059,110 | 11/1977 | Wuthrich | 604/135 |
| 4,269,185 | 5/1981 | Whitney et al. | 604/135 |
| 4,278,149 | 7/1981 | Gittler | 185/39 |
| 4,300,554 | 11/1981 | Hessberg et al. | 604/135 |
| 4,478,313 | 10/1984 | Wakase | 185/DIG. 1 X |

Primary Examiner—Allan D. Herrmann
Attorney, Agent, or Firm—Lieberman, Rudolph & Nowak

[57] ABSTRACT

A mechanical drive system for driving a syringe, or other fluid infusion system, over extended period of times, which drive system also provides manual advance and quick release features. Manual advance and quick release is selectively provided by mechanically decoupling the gear train from the syringe drive mechanism.

5 Claims, 2 Drawing Figures

FAIL-SAFE MECHANICAL DRIVE FOR SYRINGE

BACKGROUND OF THE INVENTION

This is a continuation-in-part application of Ser. No. 620,936, filed June 15, 1984, now U.S. Pat. No. 4,602,700 entitled Fail-Safe Mechanical Drive for Syringe, by Anthony W. Szabo.

This invention relates generally to mechanical drive systems, and more particularly, to an improved spring drive system which is particularly suited for driving a syringe or other fluid infusion system over extended periods of time and also providing manual advance and quick release features.

Known dispensers for infusing small doses of medical fluids over long periods of time are either bulky, and therefore not easily transportable, or powered by electric motors. Motor operated infusion systems require a source of power, such as electrical line power which confines the patient during the treatment, or batteries which are not reliable over long periods of time. Moreover, battery operated systems require the patient to maintain a relatively fresh supply of batteries, since batteries have limited shelf lives.

It is a further problem with electrically operated dispenser systems that sophisticated and expensive insulation systems are required to prevent the introduction of even minute amounts of electrical energy into the vascular system of a patient. It is now known that even small amounts of electrical energy, illustratively on the order of microamperes, can adversely affect a patient's heart. Thus, in addition to affording only short periods of unattended operation, battery power infusion systems may be dangerous to the patient, particularly if the device is subject to wet conditions.

Some of the problems noted hereinabove associated with electrically operated dispenser systems are overcome by utilizing mechanical drive arrangements. Generally, the mechanical drive arrangements, in combination with a syringe, provide an infusion pump driven by a clock mechanism. The clock mechanisms are essentially of a conventional type wherein a plate-to-plate gearing system is provided with torque by a wound spring. The rate of rotation of the system, and consequently the rate of fluid infusion, is controlled by a conventional balance wheel and escapement system.

In addition to overcoming the disadvantages of electrical systems, mechanical drive systems provide all of the known economic advantages of time-released infusion systems. Thus, such mechanical systems permit continuous injection to the patient, thereby reducing labor requirements of the hospital staff. Additionally, the automatic infusion systems substantially reduce the possibility of human failure, such as those which are produced when patient care personnel neglect or otherwise do not maintain prescribed injection schedules. Additionally, such mechanical systems provide the medical advantages of continuous injection, over cyclic injections, which conform more closely to the characteristics of fluid production systems within the patient.

An important feature with mechanical drive systems for time-released infusion systems is fail-safe apparatus to prevent catastrophic failure with attendent rapid release of the fluid being administered. In U.S. patent application, Ser. No. 620,936, now U.S. Pat. No. 4,602,700 filed June 15, 1984, entitled Fail-Safe Mechanical Drive for Syringe, by Anthony W. Szabo, and assigned to the same assignee as is the instant invention, such fail-safe apparatus is described. It is understood that such fail-safe apparatus, as is described in Ser. No. 620,936, now U.S. Pat. No. 4,602,700 may be incorporated in the device of the instant invention and the teachings of Ser. No. 620,936 are hereby incorporated herein by reference.

Although the device of Ser. No. 620,936, now U.S. Pat. No. 4,602,700 has many advantages over prior art syringe drive systems, that device did not provide for two important features. First, it is often necessary with such a syringe drive system, that medical personnel have the ability to manually advance the syringe plunger. Mechanical advance is important where a short term increase in the amount of fluid being administered is required, for example, in emergency situations, or to determine the patient's response to such a short term increase. A second important feature, not found in the device of Ser. No. 620,936, now U.S. Pat. No. 4,602,700 is the ability to manually release the driving mechanism from the syringe, such that an empty syringe can be easily removed and a replacement syringe installed, or a syringe may be removed prior to injection of the full amount of medication contained within the syringe. Manual release may also be important during emergency situations. The instant invention advantageously provides these features, as well as the additional feature of an audible "click" when the driving mechanism is wound, or when the syringe plunger is manually advanced.

It is, therefore, an object of this invention to provide a medical fluid infusion system which is inexpensive and simple to manufacture.

It is another object of this invention to provide a drive system for a syringe which is small, lightweight, portable and easily attached to a patient.

It is also an object of this invention to provide a fluid dispensing system which is reliable over extended periods of operation.

It is also another object of this invention to provide a drive arrangement for a medical fluid dispensing system which does not require an external power source.

It is a yet further object of this invention to provide a medical fluid infusion system which does not require batteries for performing the fluid infusion function.

It is still a further object of this invention to provide a mechanical drive system which can provide a driving force at a controlled displacement rate.

It is additionally an object of this invention to provide a drive arrangement for a syringe utilizing only mechanically stored energy for performing the drive function.

It is yet another object of this invention to provide the use of a mechanically driven syringe with the ability to manually advance the syringe plunger.

It is additionally a further object of this invention to provide the ability to manually release the driving mechanism for a mechanically driven syringe.

SUMMARY OF THE INVENTION

The foregoing and other objects are achieved by the instant invention which provides a drive arrangement which is particularly suited for driving a medical fluid infusion system by providing a rate controlled output displacement. Preferably, the drive arrangement is provided with a rotary drive means which provides a driving torque to a first shaft. In a preferred embodiment, the rotary drive means is provided with a spring member which is wound to store the energy which will be used to perform the driving function. A first drive gear and a first pinion gear are arranged coaxially on the first shaft. A second, or output, shaft is provided with a second drive gear and a second pinion gear, with the second drive gear communicating meshingly with the first pinion gear. The second pinion gear, in turn, communicates meshingly with a transport rack, mechanically displacing the transport rack for movement of the plunger associated with the syringe of the fluid infusion system. In accordance with the invention, there is further provided a rate control arrangement which governs the rate of operation of the drive arrangement.

In one embodiment of the invention, there is provided a third shaft, to which is coaxially affixed a third driving gear and a third pinion gear. The third pinion gear meshingly communicates with said first driving gear and said third driving gear meshingly communicates with said rate control arrangement.

In accordance with the invention, the rate control arrangement is provided with an escapement ratchet wheel which is fixed coaxially on a ratchet wheel shaft and which, as in known escapement systems, rotates at a faster rate than the output shaft. A balance wheel shaft is provided with a balance wheel fixed axially thereon for oscillating rotatably at a substantially fixed, predetermined frequency. Additionally, a lever member is arranged on a lever shaft so as to communicate with the escapement ratchet wheel and the balance wheel shaft. The lever member is of a generally known type having a lever portion with two pin members extending orthogonally therefrom. A rotative coupling arrangement, which may include a gear reduction mechanism, rotatively couples the control gear to drive the ratchet wheel shaft. Thus, the rate of rotation of the output shaft is controlled in response to the frequency of oscillation of the balance wheel.

The rate control arrangement is provided with a frequency control system which governs the predetermined frequency of oscillation of the balance wheel. In one embodiment, the frequency of oscillation is governed to an extent by a spiral spring which is fixed substantially coaxially with the balance wheel shaft, and there is further provided a mechanism for adjusting the tension force in the spiral spring. Adjustment of the mechanism, and consequently the tension force in the spiral spring, affords adjustability of the frequency of oscillation of the balance wheel, and consequently the rate of displacement of the output shaft. Overall system reliability may be enhanced by using a double drive gear and pinion arrangement as described in Ser. No. 620,936, now U.S. Pat. No. 4,602,700.

In accordance with a further aspect of the invention, the first and third shafts cooperate with slotted support members for allowing lateral displacement of said first and third driving gears and said first and third pinion gears.

Control apparatus is included for rotationally advancing the rotary drive means a first and second direction, one direction of rotation to wind a spring included within the rotary drive means and the second direction to manually advance the transport rack. When the rotary drive means is advanced in the first direction the first driving gear and pinion gear are laterally displaced resulting in mechanical decoupling of the first pinion gear from the second driving gear. Similarly, when the rotary drive means is advanced in the second direction, the third pinion gear and driving gears are laterally displaced resulting in mechanical decoupling of the third pinion gear from the first driving gear.

In accordance with a further embodiment of the invention, quick release of the transport rack is provided by rotationally advancing the control apparatus a predetermined amount in the direction of winding, whereby the transport rack is mechanically decoupled from the second pinion gear permitting the transport rack to be freely advanced or retracted by hand as required. A release button may be optionally included to maintain the control apparatus in a safe storage position.

The present invention may also be used with a fail-safe arrangement for preventing uncontrolled rotation of the escapement ratchet wheel, which does not communicate with a pinion. In a preferred embodiment, such as described in Ser. No. 620,936, a safety wheel is fixed onto the shaft of the escapement ratchet wheel so as to rotate simultaneously therewith. A centrifugal throwout mechanism is installed on the safety wheel, which mechanism is extended radially outward of the safety wheel in response to an uncontrolled rotation and acceleration of the escapement ratchet wheel. At least one stationary member is provided for engaging with the radially extended centrifugal throwout mechanism. Such an engagement prevents rotation of the safety wheel and consequently the escapement ratchet wheel.

In a further embodiment the balance wheel may be arranged in the vicinity of an opening, or window, in the case of the unit to permit visual inspection of the operation of the device.

BRIEF DESCRIPTION OF THE DRAWINGS

Comprehension of the invention is facilitated by reading the following detailed description in conjunction with the annexed drawings, in which.

DETAILED DESCRIPTION

Figure 1:
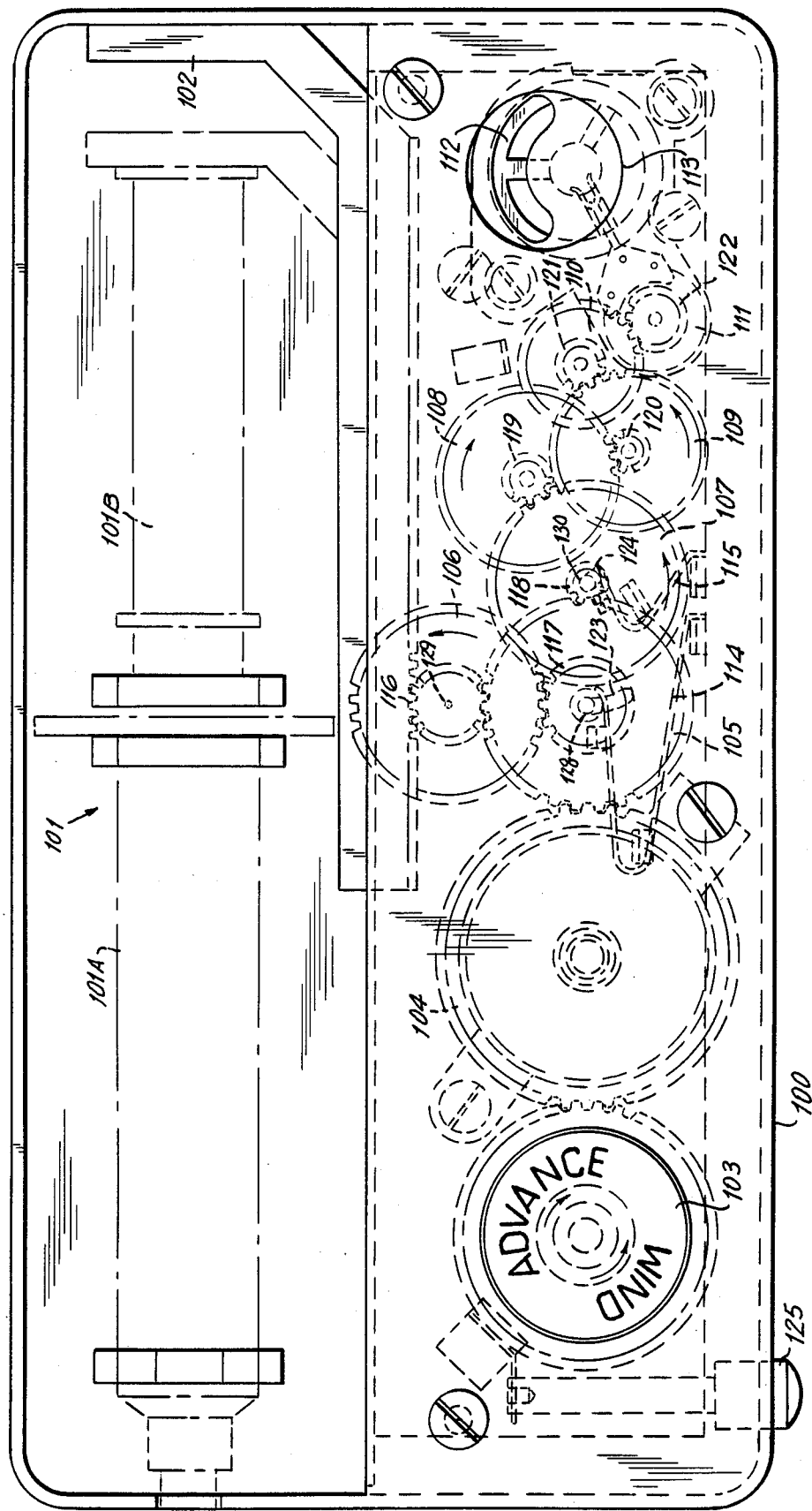
FIG. 1 is a partially schematic, simplified representation of an embodiment of the invention having an aligned gear train.

Referring now to FIG. 1, there is illustrated a simplified partially schematic representation of a mechanical drive system for use in driving a syringe or other fluid infusion system over extended periods of time, which system is particularly advantageous in providing manual advance and quick release features.

The mechanical drive system for use with a syringe or other fluid infusion system is generally shown at 100. The syringe itself, which can be, for example, a 5 cc syringe made by Becton Dickinson fastened to number 4492 Abbott Labs Tubing Infusion Set (not shown) is shown generally at 101. The syringe consists of a body portion 101A and a plunger portion shown at 101B, wherein the body portion carries the fluid to be injected into a patient, for example, and the plunger operates to force the fluid out of the syringe into the tubing for utilization by the patient. The plunger portion of the syringe is driven by rack 102, the rack being advanced by the mechanical drive system in a manner to be described hereinafter.

The driving force for the mechanical system is supplied by spring motor 104. The spring motor consists of a main spring in which mechanical energy is stored in a known manner. The spring motor is wound by wind- /advance button 103, as will be described below. Output spool 105 is mechanically connected to the spring motor and the output spool 105 in turn activates drive gear 106, which is mechanically connected to rack 102. A clockwise rotation of spool 105 results in a counter clockwise rotation of drive gear 106, which in turn advances rack 102 from right to left in FIG. 1. Right to left movement or rack 102, in turn, forces plunger 101B into the body of syringe 101 to force the fluid out of body portion 101A and into the patient.

Spools 107 through 112 comprise a speed regulation mechanism for use with the mechanical drive system of the instant invention. More particularly, spools 107, 108 and 109 consist of a gear reduction mechanism, while spools 110 and 111 are an escapement drive mechanism, which is controlled by balance wheel 112. Operation of the gear reduction mechanism, escapement drive mechanism and balance wheel, are as described in Ser. No. 620,936, now U.S. Pat. No. 4,602,700 and thus will not be described in any further detail. Spools 105, 106 and 107 rotate respectively on shafts 128, 129 and 130.

As is known in the art of clock driven mechanisms, balance wheel 112 rotates left and right as shown in FIG. 1 as the clock mechanism operates. Observing operation of the balance wheel is possible through aperture 113 which indicates to an operator of the mechanically driven syringe that the balance wheel is in fact rotating as required. Observation enhancement of the operation of the balance wheel can be achieved by, for example, color coding of the balance wheel such that operation of the balance wheel is readily observed by an operator of the system. Such a feature is advantageous for use in a medical environment in order for the operator to insure that the mechanically driven syringe is operating and injecting the necessary fluid as required.

One advantageous feature of the instant invention is the ability for an operator of this system to mechanically advance the movement of rack 102 in order to inject the selected amounts of the medicinal fluid into the patient over a short period of time for emergency use, or alternatively to determine reaction of the patient to selected amounts of fluid. Manual advance of rack 102 is accomplished with wind/advance button 103 in conjunction with spring motor 104 and the lateral displacement of spool 105 to permit such mechanical advance.

More particularly, spring motor 104 must have mechanical energy imparted thereto in order to drive the mechanical driving system shown in FIG. 1. This is accomplished by "winding" the spring motor through a counter clockwise rotation of wind/advance button 103. A counter clockwise rotation of wind/advance button 103 results in a clockwise rotation of the circumferential portion of spring motor 104. In a manner well known in the art such a clockwise rotation serves to impart mechanical energy to the spring included within the spring motor (not shown) storing mechanical energy for later use by the mechanical drive system. Advantageously, when the circumferential portion of the spring motor is driven in a clockwise direction, a resultant force is applied to spool 105 which attempts to force this spool in a counter clockwise direction.

The force imparted by the operator, sufficient to wind spring motor 104 is also sufficient to overcome the mechanical displacement energy of spring 114. This action will force spool 105 in a generally downward direction in FIG. 1, allowing this spool to move away from drive gear 106, via displacement within slot 123. Slot 123 is included within the case of drive mechanism 100 and supports spool 105 via connecting pins attached to spool 105, which are coupled with slot 123. Slot 123 permits spool 105 to move away from drive gear 106, thus mechanically decoupling spool 105 from drive gear 106 during a winding operation by separating the outer gear teeth of spool 106 from the pinion gear 117 of spool 105. Accordingly, when the operator desires to impart mechanical energy to the spring motor through a winding motion, spool 105 is moved away from drive gear 106 via slot 123 to permit winding of spring motor 104 without advancement of rack 102 due to the mechanical decoupling which occurs between spool 105 and drive gear 106.

After mechanical energy has been imparted to spring motor 104, the outer gear teeth of the spring motor turns in a counter clockwise direction. This set of gear teeth interfaces with the gear teeth on spool 105 causing this spool to rotate in a clockwise direction. The outer set of gear teeth on spool 105 is mechanically coupled to the pinion gear 116 on drive gear 106. This causes the drive gear to rotate in a counter clockwise direction. Pinion gear 116 is in turn mechanically coupled to rack 102, through a series of gear teeth at the bottom of the rack. Accordingly, as drive gear 106 rotates in a counter clockwise direction, rack 102 is moved horizontally from right to left, which in turn serves to force the plunger into the body of this syringe to impart fluid to the patient.

The outer gear teeth of spool 105 are mechanically coupled to the pinion gear 118 of spool 107. As spool 105 rotates in a clockwise direction, spool 107 rotates in a counter clockwise direction. The outer gear key of spool 107 are mechanically coupled to pinion gear 119 on spool 108 with this spool rotating in a clockwise direction. The outer gear teeth on spool 108 are in turn mechanically coupled to pinion gear 120, causing spool 109 to rotate in a counter clockwise direction with the outer gear teeth on spool 109 being mechanically coupled to the pinion gear on escapement drive 110 via pinion gear 121. Escapement drive 110 rotates in clockwise direction, with mechanical coupling between the gear teeth on the escapement drive and pinion gear 112 on escapement drive spool 111. The rotation of spool 111 is controlled by operation of the balance wheel 112 in a manner well known in the art of clock driven mechanisms.

Assume now it is desired to mechanically advance rack 102 for purposes of emergency application of medicinal fluid and/or for other medical purposes. To achieve mechanical advance of rack 102 wind/advance knob 103 is turned in a clockwise direction. Turning knob 103 in a clockwise direction advances the outer ring of gear teeth on spring motor 104 in a counter clockwise direction, advancing the outer gear teeth of spool 105 in a clockwise direction, which in turn forces spool 107 in a generally downward direction along slot 124, moving this spool out of mechanical attachment with spool 105 in the same manner as described above with respect to spool 105. Mechanically decoupling spool 105 from spool 107 disconnects the speed control mechanism from spool 105 and drive gear 106. Accordingly, as advance/wind knob 103 is advanced in a clockwise direction, spool 105 is advanced also in a clockwise direction, which advances drive gear 106 in a counter-clockwise direction to manually advance rack 102. Thus, through use of the instant invention it is possible to manually advance rack 102 when needed for medical purposes Winding the mechanical drive system shown in FIG. 1 is accomplished as described above by rotating wind-/advance knob 103 in a counter clockwise direction. Winding is accomplished without engagement of the speed control mechanism and/or the drive gear by forcing spool 105 in a generally downward direction along slot 123. Similarly, manual advance is achieved by rotating wind/advance knob 103 in a clockwise direction which, as described above, through various gearing arrangements, generally forces spool 107 in a downward direction via slot 124, allowing rack 102 to be manually advanced horizontally in a right to left direction in FIG. 1. During manual advance, or winding operations, an audible "click" is heard by the operator of the device due to the mechanical coupling of the gearing teeth. Such audible feedback is assurance to the operator that the manual advance, or winding operations, are proceeding normally.

As described above, mechanical decoupling between spool 105 and spool 107 occurs during the mechanical advance mode, due to the fact that spool 107 is forced in a generally downward direction along slot 124 by the clockwise rotation of spool 105. Spool 105 also rotates in a clockwise direction during the run mode of the fluid infusion device. Mechanical decoupling does not occur during the run mode of operation because the force generated by spring motor 104, during the run mode of operation, is insufficient to overcome the force imparted by spring 115, which maintains spool 107 in mechanical coupling with spool 105. During the mechanical advance mode, additional force is imparted to the spring motor by the physical act of advancing wind-/advance button 103. This additional force overcomes the force imparted by spring 115, thereby permitting spool 107 to be forced in the generally downward direction along slot 124.

Figure 2:
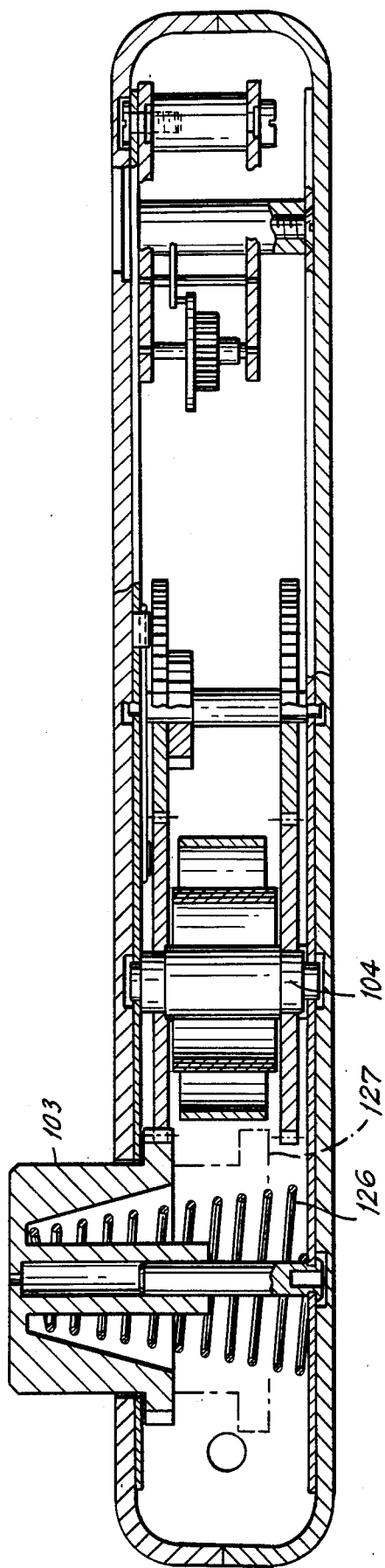
FIG. 2 is a simplified, partially schematic representation of a side view of the embodiment represented in FIG. 1.

It is to be understood that each of the gear spools shown in FIG. 1 of the instant application may be arranged in double gearing arrangements as is shown in FIG. 2 of Ser. No. 620,936, now U.S. Pat. No. 4,602,700 to achieve enhanced reliability as described in that application. In addition, the remaining safety and reliability features described in Ser. No. 620,936, now U.S. Pat. No. 4,602,700 can be incorporated into the mechanical drive system of the instant invention if desired.

In accordance with the further embodiment of the invention there is provided a safety feature which permits control knob 103 to be stored in a recessed "safety" position or extended to the wind/manual advance position. The manner in which this safety feature is provided can be illustrated by reference to FIG. 2. FIG. 2 illustrates a side view of the mechanical drive system for the syringe of the instant invention illustrating wind-/advance knob 103 and its mechanical coupling to spring motor 104. As illustrated, an upright "operate" position of advance/wind knob 103 is maintained by spring 126. Spring 126 forces knob 103 into a position adjacent to the upper portion of the syringe case during normal operation. In this position, the advance and wind functions described are accomplished through mechanical coupling between the gear teeth on the wind/advance knob and spring motor 104.

A recessed "safety" position is provided by depressing control knob 103 in a downward direction, which in turn compresses spring 126. The depressed position of knob 103 is illustrated by dotted lines 127 in FIG. 2. In this position it is understood that a release button could be incorporated within the syringe case, for example, release button 125 in FIG. 1 Release button 125, in conjunction with appropriate mechanical coupling arrangements serves to maintain control knob 103 in the recessed position until released. Such an embodiment would be useful wherein accidental winding or manual advance could occur and in addition recessing the control knob provides a "narrower" profile for the device.

In accordance with a still further embodiment of the invention, a quick release feature is provided to enable rack 102 to be rapidly disengaged from the syringe plunger to permit quick release of the syringe from the mechanical drive system. More particularly, as described above, turning control knob 103 in the "wind" direction forces spool 105 to move away from gear 106, thus mechanically decoupling spool 150 from drive gear 106. When control knob 103 is turned a predetermined amount, sufficient to achieve mechanical decoupling between spool 105 and drive gear 106, but insufficient to commence a winding operation, quick release is achieved. With quick release, rack 102 can be freely moved as required.

Although a specific embodiment of this invention has been shown and described, it will be understood that various modifications may be made without departing from the spirit of this invention.

I claim:

1. An improved mechanical drive arrangement for fluid infusion device comprising:
   rotary drive means (104) for providing a driving torque to a first shaft (128),
   means (103) mechanically coupled to said rotary drive means for rotationally advancing said rotary drive means in a first and second direction,
   a first driving gear (105) and a first pinion gear (117) fixed coaxially to said first shaft, said first shaft cooperating with slotted support members for selectively allowing lateral displacement of said first driving gear and said first pinion gear,
   a second driving gear (106) and a second pinion gear (116) fixed coaxially to a second shaft (129), said second driving gear mechanically coupled to a transport rack for providing mechanical displacement of said transport rack,
   a third driving gear (107) and a third pinion gear (118) fixed coaxially to a third shaft (130), said third shaft cooperating with slotted support members for selectively allowing displacement of said third driving gear and said third pinion gear, said third pinion gear being mechanically coupled to said first driving gear, and
   rate control means for fixing a time rate of rotation of said second shaft, said third driving gear being mechanically coupled to said rate control means.

2. An improved mechanical drive arrangement for a fluid infusion system in accordance with claim 1 wherein said transport rack is arranged adjacent to said fluid infusion system whereby mechanical displacement of said transport rack provided dispersal of fluid contained within said fluid infusion system.

3. An improved mechanical drive arrangement for a fluid infusion system in accordance with claim 2, wherein rotational advancement of said rotary drive means in said first direction laterally displaces said first driving gear and said first pinion gear, said lateral displacement resulting in mechanical decoupling between said first pinion gear and said second driving gear.

4. An improved mechanical drive arrangement for a fluid infusion system in accordance with claim 3, wherein rotational advancement of said rotary drive meanse in said second direction laterally displaces said third driving gear and said third pinion gear, said lateral displacement resulting in mechanically decoupling between said third pinion gear and said first driving gear.

5. An improved mechanical drive arrangement for a fluid infusion system in accordance with claim 4, wherein there is further provided means for mechanically decoupling said rotationally advancing means from said rotary drive means.

* * * * *